(12) United States Patent
Fearnot et al.

(10) Patent No.: US 10,485,957 B2
(45) Date of Patent: Nov. 26, 2019

(54) GUIDE MEMBERS AND ASSOCIATED APPARATUSES USEFUL FOR INTRAVASCULAR ULTRASOUND PROCEDURES

(71) Applicant: Muffin Incorporated, West Lafayette, IN (US)

(72) Inventors: Neal E. Fearnot, West Lafayette, IN (US); Peter S. McKinnis, West Lafayette, IN (US); Kem Hawkins, Bloomington, IN (US)

(73) Assignee: Muffin Incorporated, West Lafayette, IN (US)

( * ) Notice: Subject to any disclaimer, the term of this patent is extended or adjusted under 35 U.S.C. 154(b) by 1018 days.

(21) Appl. No.: 14/704,236

(22) Filed: May 5, 2015

(65) Prior Publication Data

US 2015/0320979 A1 Nov. 12, 2015

Related U.S. Application Data

(60) Provisional application No. 61/989,679, filed on May 7, 2014.

(51) Int. Cl.
| | |
|---|---|
| *A61B 8/12* | (2006.01) |
| *A61M 25/09* | (2006.01) |
| *A61B 8/00* | (2006.01) |
| *A61B 8/08* | (2006.01) |
| *A61M 25/01* | (2006.01) |

(52) U.S. Cl.
CPC .......... *A61M 25/09* (2013.01); *A61B 8/0891* (2013.01); *A61B 8/12* (2013.01); *A61B 8/445* (2013.01); *A61B 8/483* (2013.01); *A61M 25/0108* (2013.01); *A61M 2025/0177* (2013.01); *A61M 2025/09133* (2013.01); *A61M 2025/09166* (2013.01)

(58) Field of Classification Search
CPC ......... A61B 8/0891; A61B 8/12; A61B 8/445; A61B 8/483; A61M 2025/0177; A61M 2025/09133; A61M 2025/09166; A61M 25/0108; A61M 25/09
See application file for complete search history.

(56) References Cited

U.S. PATENT DOCUMENTS

| | | |
|---|---|---|
| 6,254,550 B1 | 7/2001 | McNamara et al. |
| 6,383,146 B1 | 5/2002 | Klint |

(Continued)

FOREIGN PATENT DOCUMENTS

| | | |
|---|---|---|
| JP | 2008-119523 A | 5/2008 |

OTHER PUBLICATIONS

International Application No. PCT/US2015/029229 International Search Report and Written Opinion, dated Aug. 21, 2015, 13pgs.

*Primary Examiner* — Mark D Remaly
(74) *Attorney, Agent, or Firm* — Woodard Emhardt, Henry, Reeves & Wagner LLP

(57) ABSTRACT

Described are guidewires having at least one echolucent segment, and associated apparatuses and methods. The guidewires can be combined with devices equipped with intravascular ultrasound probes and used to effectively image regions during procedures underway in the vascular environment. The echolucent segment can have one or more echogenic markers to enable detection of the segment and/or relative movement of the segment using intravascular ultrasound.

18 Claims, 5 Drawing Sheets

(56) References Cited

U.S. PATENT DOCUMENTS

| | | |
|---|---|---|
| 6,475,226 B1 | 11/2002 | Belef et al. |
| 6,673,015 B1 | 1/2004 | Glover et al. |
| 8,382,674 B2 | 2/2013 | Webler |
| 2004/0106891 A1* | 6/2004 | Langan ............ A61M 25/0084 604/19 |
| 2010/0101822 A1* | 4/2010 | Bunker ................ C08F 255/02 174/110 SR |
| 2011/0021924 A1 | 1/2011 | Sethuraman et al. |
| 2012/0095434 A1 | 4/2012 | Fung et al. |
| 2012/0228273 A1 | 9/2012 | Mishima et al. |
| 2014/0257090 A1* | 9/2014 | Fischer, Jr. ............ A61B 8/42 600/424 |

* cited by examiner

US 10,485,957 B2

GUIDE MEMBERS AND ASSOCIATED APPARATUSES USEFUL FOR INTRAVASCULAR ULTRASOUND PROCEDURES

The present application claims the benefit of U.S. Provisional Patent Application Ser. No. 61/989,679, filed May 7, 2014, which is hereby incorporated by reference in its entirety.

BACKGROUND

The present invention relates generally to medical devices and procedures, and in particular aspects, to vascular guidewires and combinations thereof with other vascular devices, such as catheters, that can be beneficially used in animal and human patients when conducting procedures that employ intravascular ultrasound (IVUS) for imaging.

Guidewires useful for intravascular procedures can be constructed using various materials and techniques. For example, guidewires can be constructed of segments of metallic wire formed into coils or strands, or both. Wire guides may also be coated with one or more of a wide range of coatings, such as for example, Polytetrafluoroethylene (PTFE) for reduced friction, or an anticoagulation agent like Heparin to reduce blood clotting.

However, metal wire guides are highly reflective to ultrasound because the characteristic acoustic impedance of metallic substances causes substantially all of the sound waves to reflect off the device rather than passing through. Therefore, when metal guidewires are inserted into a patient and imaged using ultrasound imaging devices, various artifacts are routinely observed which can obscure important imaging features. For example, when a metallic guidewire is in use, a bright dot may be observed with a large shadow behind the wire.

These artifacts may be especially severe in IVUS imaging. Due to space, size, and cost (i.e. one time use) limitations, IVUS transducers may have lower overall performance as compared to conventional transcutaneous transducers. Therefore, artifacts may be more pronounced further degrading image quality. The artifacts may be especially severe if the wire is close to the IVUS transducer further reducing opportunities to obtain usable, and perhaps critically important, clinical information from the ultrasound image.

SUMMARY

The embodiments disclosed are directed toward guide members, such as guidewires and wire guides having similar function and purpose to those discussed above that are useable in conjunction with intravascular ultrasound procedures but which reduce or eliminate visual artifacts caused by metallic or other echogenic materials. Also included are modes of construction as well as examples of techniques and descriptions of their use.

Embodiments described include guidewires that are at least partially echolucent presenting reduced visual interference in an ultrasound image when the echolucent portion is present within the imageable region. Ultrasonic waves preferably resonate in a frequency range as low as 20 khz or as high as 4 Ghz, with lower or higher frequencies possible as well depending on factors such as the imaging device used and the clinical objectives to name a few. Sound waves at any frequency cause the molecules of a physical substance they pass through (a "medium") to vibrate. The density and the speed at which sound travels in the medium dictates how easily sound energy can pass through the medium. As sound waves pass through one medium to another different medium, the energy waves can change velocity causing some of the sound energy to be reflected off the new medium and some to pass through at a new velocity.

For example in a clinical setting, as sounds waves move away from an ultrasonic transducer and through a human or animal, they may encounter several substances along the way such as muscle, bone, various liquids, air or other gases, and the like. Various clinical instruments and apparatus (such as a guidewire) may also be in the path of these waves. As the sound waves travel from one medium to another, such as from human tissue, through bodily fluids, through a guidewire, perhaps through bodily fluids again, and into the same or other human tissue behind the guidewire, the sound waves change speed at the interfaces between the different media. This speed change causes some of the sound energy to be reflected back toward the transducer, while some of the sound energy continues on away from the transducer. Generally speaking, as more sound energy is reflected back to the transducer, the reflecting medium generally appears more distinctly in the resulting ultrasound image. Therefore, materials that are "echolucent" appear less distinctly because they allow sound waves to travel through them causing fewer echoes. Materials that are "echogenic" allow fewer sound waves to travel through and cause more sound energy to be reflected. For example, as disclosed below, materials reflecting about the same amount of sound energy as soft tissue and fat result in few if any echoes being returned from these materials when they are used in a medical apparatus such as a guidewire inserted in the body adjacent to soft tissue and fat.

Different materials can be chosen to adjust the "echolucence" of a device because doing so changes the characteristic acoustic impedance of the device. The characteristic acoustic impedance of a material or medium is an inherent property of that particular medium and is the product of the density of the medium and the speed of sound in the medium when no sound waves are traveling in it. Measured in Rayleigh (Rayl), 1 Rayl equals 1 newton-second per cubic meter or 1 kg/s·m². Therefore the materials used in the construction of a guidewire or other similar apparatus may be varied to adjust the characteristic acoustic impedance of the material, thereby changing the ratio of sound energy passing through the material to the sound energy reflected by it. This can result in a guidewire or similar apparatus creating few if any resulting echoes under ultrasonic imaging thus reducing the visibility of the device. Reduced visibility caused by using echolucent materials makes it possible to image structures behind the guidewire (that is structures opposite the guidewire from the transducer) because sound energy can reach the more distal media by passing through the guidewire both after leaving the transducer and again on the way back to it.

Various materials and modes of construction can be used to vary the echolucent properties of a guidewire or other such apparatus as disclosed. In one example, echogenic markers and marker regions are included along with the echolucent regions of the guide members. These echogenic markers may, for example, be constructed from a medium having a characteristic acoustic impedance that differs widely from that of human or animal flesh. For instance, the characteristic acoustic impedance of air at about room temperature is about 415 Rayl while the characteristic acoustic impedance of certain human or animal tissue can be in the range between about 1.5 to about 1.7 MRayl (or million Rayl)—over 3800 times higher. Thus, examples of guidewires with echogenic markers include guidewires made at least partially of materials having a characteristic acoustic impedance that is approximately equal to that of human flesh where the material also encapsulates or includes one or more voids containing air. Under ultrasound imaging, the voids (i.e. "bubbles", or "markers") enclosed in the material are more visible in the resulting image than the surrounding material which can be substantially invisible, or at least its visibility can be substantially reduced.

Also disclosed are other materials, forms, and configurations besides air bubbles that could be used as markers, this being merely one example. Metallic flakes, elongated strips, beads, and other arrangements of marking elements or groups of elements embedded within or coupled to an echolucent guide member, or guide member portion, can therefore assist clinicians in tracking and positioning the guide members during imaging while minimizing unwanted artifacts. Also disclosed are embodiments of guide members used in conjunction with two dimensional and three dimensional intravascular ultrasound imaging devices.

BRIEF DESCRIPTION OF THE FIGS.

DETAILED DESCRIPTION

Figure 1:
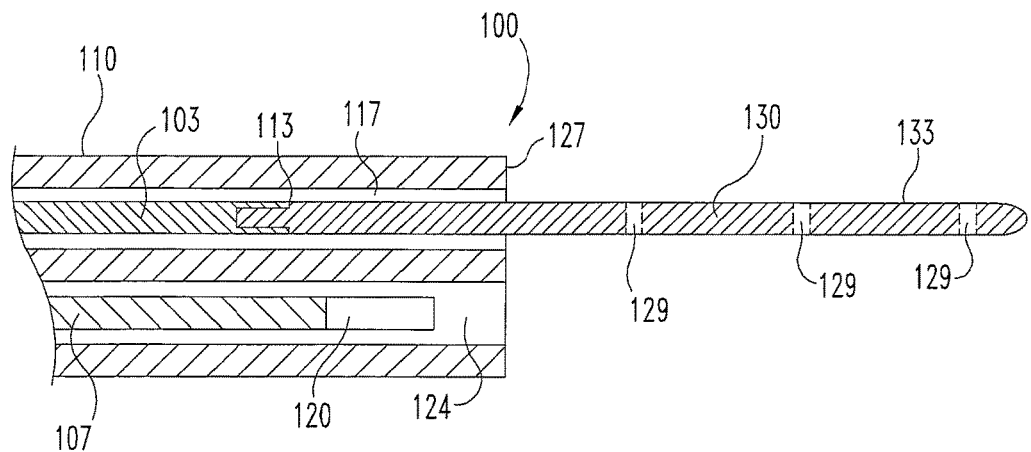
FIG. 1 is a longitudinal cross-sectional view of the distal end of one example of a guide member and other apparatuses useful in intravascular ultrasound procedures

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Illustrated in FIG. 1 at 100 is one embodiment of a guide member 133 along with other associated apparatuses useful for intravascular ultrasound procedures in an animal or human patient. Guide member 133 is shown having a segmented arrangement of individual portions or segments joined together, these portions themselves may then also include other portions or segments as well depending on the materials used, the mode of construction, and the intended use. In the embodiment shown in FIG. 1, a first guide body portion 130 forming the distal end of guide member 133 is coupled to a second guide body portion 103, with the two segments joined to one another at joint 113. First guide body portion 130 has one or more longitudinally spaced discrete echogenic markers 129 interspersed along its length which are operable to appear during ultrasonic imaging procedures. Guide member 133 may be positioned within a first lumen 117 and can extend beyond distal end 127 of an elongate carrier body 110. Elongate carrier body 110 can serve various functions such as maintaining an association between guide member 133 and an intravascular ultrasound probe 107 positioned within a second lumen 124. By maintaining this association, guide member 133 can aid in maneuvering intravascular ultrasound probe 107 into position within the patient's body.

Intravascular ultrasound probe 107 positioned within second lumen 124 has at its distal end an ultrasonic transducer 120 which is operable to emit ultrasonic energy and detect the reflected energy for the purpose of performing ultrasonic imaging of interior spaces of a patient's anatomy such as organs, blood vessels, and the like. Ultrasonic transducer 120 is preferably positioned distal to joint 113 so that ultrasonic energy emitted from ultrasonic transducer 120 passes through carrier body 110 and first guide body portion 130 but not through second guide body portion 103.

Elongate carrier body 110 can be constructed of any material suitable for intravascular introduction and navigation through blood vessels, organs, and other structures within a patient's body. Suitable materials include, but are not limited to, polyurethane, nylon, polyethylene, and silicone. Preferably elongate carrier body 110 includes echolucent materials to reduce or substantially eliminate sound energy reflected by the echolucent portion of carrier body 110. By including echolucent material in elongate carrier body 110 in those regions where ultrasonic energy resonates from transducer 120, ultrasonic waves can pass substantially unimpeded through carrier body 110 allowing the tissue surrounding carrier body 110 to be imaged.

One embodiment of elongate carrier body 110 is a catheter having multiple lumens extending through some or all of the length of the catheter and exiting at or near the catheter's distal end. In this embodiment, the catheter acts to keep guide member 133 and intravascular ultrasound probe 107 properly positioned relative to one another such that guide member 133 can be used to help advance elongate carrier body 110. Elongate carrier body 110 can then be useful for properly advancing intravascular ultrasound probe 107 to its intended region within the body. Other embodiments of elongate carrier body 110 include catheters having an intravascular ultrasound probe 107 embedded in, or otherwise coupled with, the catheter itself.

FIG. 1 illustrates a first guide body portion 130 that includes an echolucent material. An echolucent material includes any material having a characteristic acoustic impedance substantially similar or about equal to the characteristic acoustic impedance of the surrounding material (e.g. bone, blood, muscle, bodily fluids, or other human or animal anatomical features of interest). Thus as sound waves pass through from the surrounding media and through first guide body portion 130, the change in speed of the high frequency sound waves is minimized resulting in fewer echoes being returned to transducer 120 from guide body portion 130. The results include ultrasound images where guide body portion 130 may be substantially or completely invisible. This allows the surrounding tissue or other anatomical structures of interest to be imaged rather than guide body portion 130.

In one example, the echolucent material in first guide body portion 130 may have a characteristic acoustic impedance of between about 1.5 MRayl and about 2.2 MRayl, which is approximately the range of characteristic acoustic impedances for many types of human or animal tissue. Examples of such echolucent materials include Polyethylene (PE), Polymethylpentene, and Ethyl Vinil Acetate. In another example, the echolucent material in first guide body portion 130 may have a characteristic acoustic impedance of between about 1 MRayl and about 5 MRayl, although such a material may cause reduced performance making guide body portion 130 more visible during ultrasonic imaging procedures. Examples of such materials include Acrylic, Polyvinyl Chloride (PVC), Polycarbonate, Nylon, Polystyrene, Vinyl, and Acrylonitrile Butadiene Styrene (ABS). First guide body portion 130 may, for example, include a polymeric material having a density in the range of 0.5 grams/cc to 3.5 grams/cc. In another embodiment, first guide body portion 130 includes polyethylene or another polymeric material having a density in the range of about 0.8 grams/cc to about 1.1 grams/cc.

In other embodiments, first guide body portion 130 may include other echogenic structures or substances to modify the number and strength of reflected sound waves. Making a first guide body portion 130 disappear entirely from the resulting image may be undesirable and may result in a substantial reduction or complete loss of positional feedback. As a result, the clinician may, in such situations, be unable to properly maneuver and position first guide body portion 130 during the ultrasonic imaging procedure.

Providing positional feedback using the ultrasonic imaging system may be achieved in various ways such as through the use of echogenic markers or marker regions as discussed below. However, it may also be advantageous to optionally include an echo-opacifier into the polymeric material used to construct first guide body portion 130 to precisely control its characteristic acoustic impedance. Examples of echo-opacifiers that might be used include tungsten nanoparticles, glass or ceramic beads, or gas filled voids or other similar structures or materials included with guide body portion 130. By varying the concentration, placement, size and other aspects of the additives or structures, the acoustic impedance and corresponding echogenicity and echolucence may be modified to control the resulting appearance of first guide body portion 130 in an ultrasound image.

The echolucence may also be reduced and echogenicity increased by using materials with characteristic acoustic impedances that differ from the characteristic acoustic impedance of the human or animal tissue in the surrounding region. For example, constructing a guide body portion 130 from PVC, which has a characteristic acoustic impedance of about 3 MRayl, can provide additional visibility of first guide body portion 130 for the clinician while still allowing some of the sound waves to pass through making it still possible to image the area behind guide body portion 130.

In other embodiments, other materials or structures may also be included in first guide body portion 130 to modify its visibility with respect to other types of imaging technologies such as to make first guide body portion 130 partially or completely radio opaque. Such an embodiment may be useful where two different imaging technologies (e.g. ultrasonography and radiography) are used during the same procedure. For example, first guide body portion 130 may be constructed of Polyethylene (which has a characteristic acoustic impedance of about 1.73 MRayl) that also includes Barium sulfate or other similar radio-opacifier. The resulting guide wire may therefore be echolucent returning very few echoes to transducer 120 presenting a reduced or minimally visible ultrasound image while also being visible during X-ray imaging.

Tracking the position of first guide body portion 130 may also be achieved by including one or more echogenic markers 129 spaced longitudinally along the long axis of first guide body portion 130. Although FIG. 1 illustrates a first guide body portion 130 having three echogenic markers 129, the precise number of echogenic markers 129 shown in FIG. 1 is only illustrative. In some embodiments only one echogenic marker 129 may appear while in other embodiments numerous markers, or groups of markers, may be included. (See FIGS. 5A through 7C and the accompanying description below for examples.)

Echogenic markers 129 include individual flakes of metal of the proper size and shape affixed to or embedded within guide member 133, metal beads or plugs embedded within guide member 133, metal strands or fibers adhered to the external surface of guide member 133, or metal strands or fibers embedded within the interior of guide member 133. Various metals might be used as an echogenic material for echogenic markers 129. For example, substances such as stainless steel or a nickel and titanium alloy like nitinol might be formed into flakes, strands, fibers, or other forms and embedded, attached, adhered, or otherwise coupled and included with guide member 133 to form echogenic markers 129.

Other embodiments of echogenic markers 129 include a first guide body portion 130 of guide member 133 where each echogenic marker 129 includes one or more echogenic structures such as one or more empty or gas filled spaces or "bubbles" at the proper positions along the length of guide member 133. These bubbles may be of various sizes such as large and individually positioned bubbles where each individual bubble serves as an echogenic marker 129, or individually small bubbles arranged together to form rings, lines, or other shapes serving as echogenic markers 129 (See FIGS. 5C-7B). The bubbles themselves may define an empty space containing a near vacuum, or be filled with a small quantity of gas, or contain any type of matter having a characteristic acoustic impedance that substantially differs from the surrounding tissue.

Other embodiments of guide member 133 are envisioned as well. For example, it is envisioned that in another embodiment of guide member 133 no joint 113 exists. In this embodiment, first guide body portion 130 is a single first guide body segment formed of echolucent material and has associated with it at least one echogenic marker 129. In this embodiment, no concern need be given to the positioning of guide member 133 relative to ultrasonic transducer 120 (discussed in greater detail below with regard to FIGS. 2 and 4) because all of guide member 133 is echolucent and no second guide body portion 103 is included. One example of such a guide member 133 is a guidewire for use in an intravascular ultrasound procedure formed from an echolucent material with one or more echogenic markers associated with the guidewire, preferably at or near its distal end. One example of such a guidewire is a polyethylene guidewire having a single echogenic marker formed from a nitinol bead embedded within the guidewire near its distal end.

In the embodiment illustrated in FIG. 1, second guide body portion 103 may be formed from an echogenic material, or other similar material. In one preferred embodiment, second guide body portion 103 includes a metal or metallic substance such as a material containing a combination of polymeric (or other nonmetallic) and metallic fibers. Examples of a guide member 133 having echogenic properties include a guidewire constructed of strands or coils of stainless steel or nitinol, or other similarly echogenic material, having a segment coupled to the distal end constructed from Polyethylene or other similar echolucent material.

Figure 2:
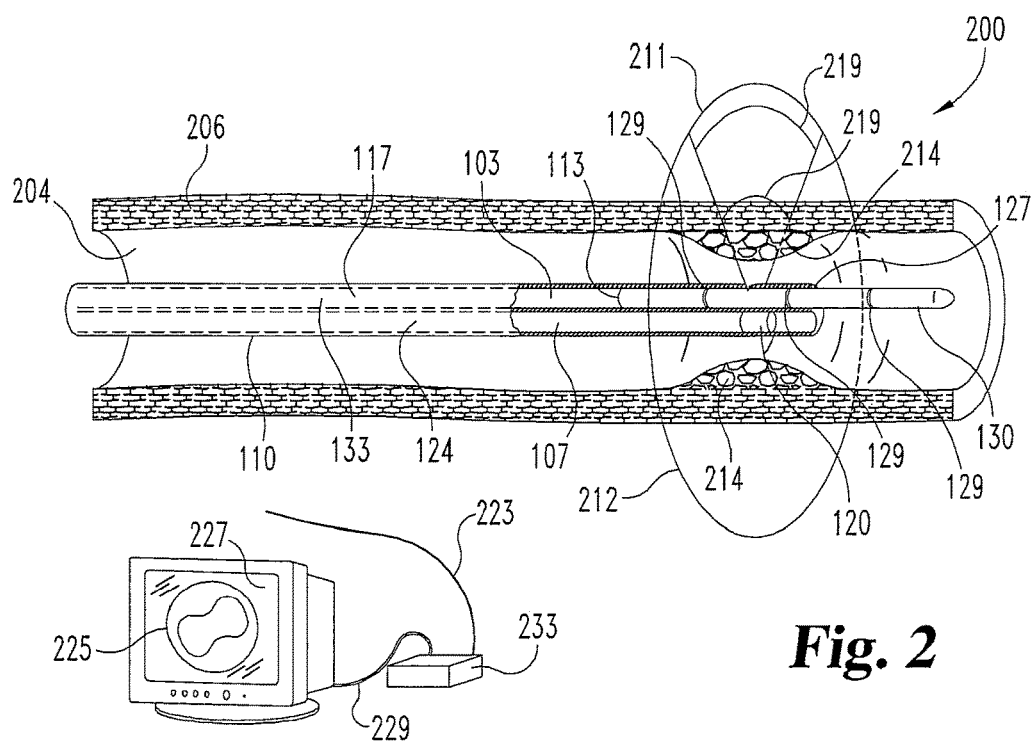
FIG. 2 is a perspective partial cut-away view of the devices from FIG. 1 introduced within a vascular lumen and connected to imaging equipment.

Shown in FIG. 2 is an illustration of the apparatus illustrated in FIG. 1 in use during a procedure such as an intravascular procedure to image internal areas of a human or animal patient's body. Elongate carrier body 110 is shown in FIG. 2 introduced into a vascular vessel 200 having a vascular wall with a vascular wall 206 and a vascular blockage 214. Guide member 133 is shown projecting from the distal end of elongate carrier body 110 beyond intravascular ultrasound probe 107. As ultrasonic transducer 120 of intravascular ultrasound probe 107 is energized, ultrasonic energy waves 219 begin to radiate outwardly from intravascular ultrasound probe 107 through elongate carrier body 110 into and through an imageable region 212 which is external to elongate carrier body 110 and extends through the contents of vascular lumen 204, through vascular wall 206 and perhaps beyond. Depending on the particular implementation of intravascular ultrasound probe 107 in use, the imageable region may at any time include only a partial imageable region 211 of the total imageable region 212. Therefore, some embodiments of intravascular ultrasound probe 107 must be rotated repeatedly to obtain updated views of the entire imageable region 212. In one embodiment of intravascular ultrasound probe 107, updated views of the imageable region 212 are generated automatically by an ultrasonic transducer 120 having an array of one or more radiating elements configured to electronically sweep imageable region 212 without rotating ultrasonic transducer 120. In another embodiment of intravascular ultrasound probe 107, updated image data from imageable region 212 is generated by manually rotating ultrasonic transducer 120 such as by the clinician applying rotational torque on ultrasound probe 107, or by the use of a rotational device such as an electric motor coupled to ultrasound probe 107.

Regardless of how much or little of imageable region 212 is scanned or imaged at any given time, in this embodiment of intravascular ultrasound probe 107, the imageable region is a substantially two-dimensional cross-sectional slice which can include the vascular lumen 204 and its contents, vascular wall 206, as well as any abnormalities in vascular wall 206 such as vascular blockage 214. The cross-sectional slice is imaged at the approximate location of ultrasonic transducer 120 as indicated by the location of imageable region 212. It should be noted that although FIG. 2 indicates an apparent maximum extent of the imageable region 212, no assumption should be made from the illustration as to whether such a maximum range exists, nor how far it extends. Many factors determine the sensory capabilities of an ultrasonic imaging probe in general. Among them are the unique attributes of a particular patient, the particular location within the body relative to various organs and structures, the power and frequency of the emitted energy, as well as various other operational settings of the particular embodiment of ultrasonic transducer 120 in use. Thus no particular assumption should be made as to the degree to which imageable region 212 extends beyond the walls of elongate carrier body 110.

The result of penetrating imageable region 212 with ultrasonic energy waves 219 and detecting the return echoes may include image data indicating various information such as the extent to which vascular blockage 214 extends into vascular lumen 204, and the type of material vascular blockage 214 is composed of, to name a few examples. In order to collect this information, elongate carrier body 110 is coupled to an image data interface device 233 through a transducer link 223 such as a data cable or wireless data link that is operable to transmit data from transducer 120 to data interface device 233. Data interface device is also coupled to image data display device 227 by a connecting member 229 such as a data cable, wireless data link, or other similar device able to transmit data to data display device 227.

Return echoes from objects within the imageable region 212 are converted to a data stream by image data interface device 233 and the data is then passed to image data display device 227 where the data is processed into image data 225 and displayed as an image of imageable area 212 for the clinician to view, review, save for the patient to view later, archive in medical records, or use for other purposes.

In some embodiments, image data display device 227 is a general purpose computer capable of operating specialized software able to capture data received through connecting member 229 from image data display device 227, process the data into one or more images, and display this image data 225. In other embodiments, image data display device 227 is a specialty built computer designed and built for only the purpose of capturing image data from connecting member 229 and processing the data into image data 225. In either case, image data 225 is processed into any of various visual representations such as still frames containing individual snapshots of imageable region 212, or as a stream of image data 225 appearing on image data display device 227 as a moving image. In the case of a moving image, image data 225 is preferably refreshed with new data from imageable region 212 at a rate of greater than 15 frames per second, more preferably greater than 20 frames per second, and most preferably 30 frames per second or more.

The use of guide member 133 is shown in FIG. 2 where guide member 133 has been introduced into the body along with elongate carrier body 110 and intravascular ultrasound probe 107. It is commonly the case that guide member 133 is introduced into the body first, followed by elongate carrier body 110, possibly then followed by intravascular ultrasound probe 107. It is also common for guide member 133 to be advanced some distance through the body ahead of elongate carrier body 110 before the elongate carrier body and intravascular ultrasound probe 107 are then advanced together as well. The sequence of advancing guide member 133 followed by elongate carrier body 110 is then repeated until the area of interest is reached, or until the procedure is complete for in some cases the purpose of advancing intravascular ultrasound probe 107 is to obtain image data throughout the journey. Navigation of guide member 133 throughout this process is frequently aided by other imaging techniques such as fluoroscopy, MRI imaging, and the like. Upon arriving at the area to be imaged, or possibly in some cases throughout the journey, guide member 133 extends beyond distal end of elongate carrier body 110 as shown in FIG. 2. Intravascular ultrasound probe 107 can then be activated (if it is not already active) causing image data 225 to begin appearing on image data display device 227.

As can be seen in FIG. 2, joint 113 can be positioned proximal to ultrasonic transducer 120 and is therefore proximal to imageable region 212. By this relative positioning of guide member 133 and intravascular ultrasound probe 107, first guide body portion 130 comprising an echolucent material is the only portion of guide member 133 within imageable region 212. As a result, ultrasonic energy emitted by ultrasonic transducer 120 passes through first guide body portion 130 rather than being reflected by it, and therefore first guide body portion 130 does not substantially interfere with image data 225. This result is preferable insofar as it avoids extraneous information appearing within image data 225 that may obscure more important information, make important information more difficult to discern, or otherwise interfere with image data 225. However, if guide member 133 is positioned such that joint 113 is distal to ultrasonic transducer 120, second guide body portion 103 will be positioned within imageable region 212. Extraneous information will then begin to appear in image data 225 because second guide body portion 103 is composed of an echogenic material that will not allow some or all of the ultrasonic energy emitted by ultrasonic transducer 120 to pass through it thus causing interference to appear within with image data 225.

In some cases it may be preferable for the clinician to have a visual cue appearing within image data 225 indicating the location of the echolucent portion of guide member 133 within vascular lumen 204. This potential need is facilitated by a plurality of longitudinally spaced echogenic markers 129 which may also be implemented as marker regions having groups of markings arranged in various patterns such as a helix, lines, stripes, dots and the like (examples of various embodiments of echogenic markings are shown in FIGS. 5A through 7C). Ultrasonic energy 219 passes through first guide body portion 130 but is reflected back to intravascular ultrasonic transducer 120 by any echogenic markers 129 in the path of emitted ultrasonic energy 219. Because of their small size relative to guide member 133, echogenic markers 129 appear in image data 225, and therefore indicate the position of first guide body portion 130 without causing substantial visual interference. Echogenic markers 129 therefore aid the clinician in maneuvering guide member 133 while still maintaining visual cues within image data 225 that do not cause substantial visual interference.

Depending on the type of ultrasonic transducer used, the image data collected may be a series of two dimensional cross-sectional slices captured at various points within the patient's body and then displayed. In other embodiments, the ultrasonic transducer may be capable of generating image data which includes a three dimensional or volumetric representation of the area of interest. An example of a device having these capabilities is illustrated in FIG. 3 and shown in operation in FIG. 4 and described below.

Figure 3:
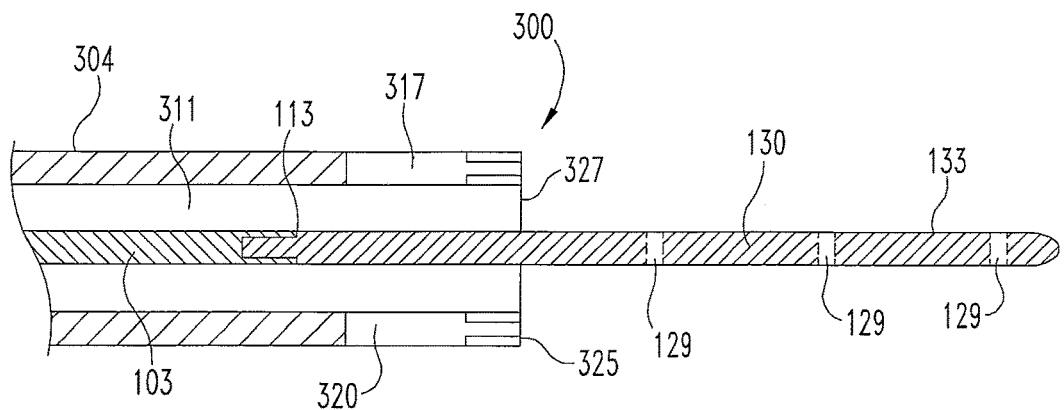
FIG. 3 is a longitudinal cross-sectional view of the distal end of the guide member from FIG. 1 in use with still other apparatuses useful in intravascular ultrasound procedures.

Illustrated in FIG. 3 at 300 is an example of use the guide member 133 illustrated in FIG. 1 in conjunction with a forward-looking ultrasound transducer. Guide member 133 extends beyond the distal end of an elongate carrier body 304 having an internal lumen 311 and an intravascular ultrasound probe 320 at distal end 327. Intravascular ultrasound probe 320 includes a forward-looking transducer array 325 arranged annularly around distal end 327 of elongate carrier body 304. Guide member 133 extends past forward-looking transducer array 325 thereby allowing ultrasonic energy emanating from forward-looking transducer array 325 to pass through and around first guide body portion 130. As in FIGS. 1 and 2, joint 113 appears proximally to intravascular ultrasound probe 320 such that second guide body portion 103 composed of echogenic material is proximal to forward-looking transducer array 325 while first guide body portion 130 composed primarily of echolucent material passes through distal end 327 and is distal to forward-looking transducer array 325. Rather than an ultrasonic transducer that radiates ultrasonic energy laterally through the side walls of the elongate carrier body 304 (as in FIGS. 1 and 2), an array of multiple transducers are arranged to emit ultrasonic energy forward of transducer array 325 toward the region distal to distal end 327.

One embodiment of intravascular ultrasound probe 320 contains an array of Capacitive Micromachined Ultrasonic Transducers (CMUT) arranged in a forward-looking transducer array 325 such that ultrasonic energy is directed longitudinally ahead of transducer array 325 and carrier body 304. Ultrasonic energy is emitted and detected by elements in the array 325 which are controlled by integrated circuits 317. Other types of transducers and transducer arrays may be used as well such as piezoelectric transducers. In this example of elongate carrier body 304, the CMUT transducer array is positioned at the distal end of a single lumen catheter. Other configurations are also envisioned such as multi-lumen catheters, or a forward-looking transducer array positioned next to the distal end rather than annularly around it.

Figure 4:
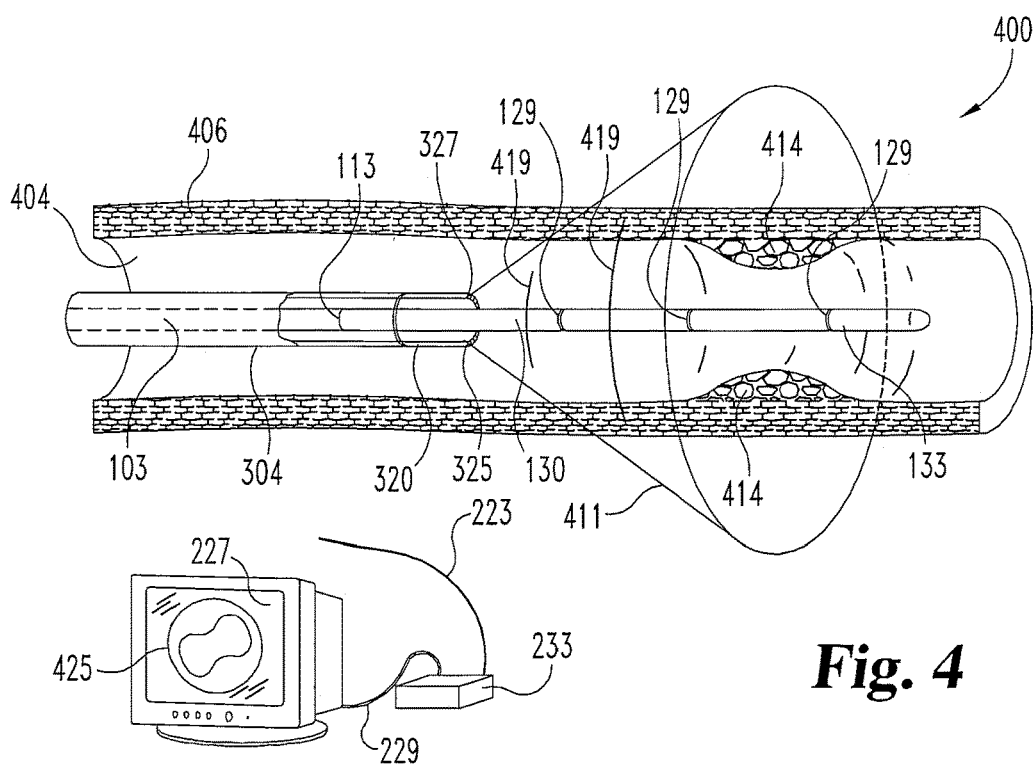
FIG. 4 is a perspective partial cut-away view of the devices from FIGS. 1 and 3 introduced within a vascular lumen and connected to the imaging equipment of FIG. 1.

FIG. 4 illustrates how the devices shown in FIG. 3 could be used in an imaging procedure such as intravascular imaging of a partially blocked internal lumen in a patient such as a vascular vessel. A blood vessel 400 appears in FIG. 4 which is similar to the vessel appearing in FIG. 2. Blood vessel 400 has a vascular lumen 404, within which has been introduced elongate carrier body 304 having an intravascular ultrasound probe 320 coupled to its distal end. Intravascular ultrasound probe 320 includes a forward-looking transducer array 325. Ultrasonic waves 419 are generated by forward-looking transducer array 325 creating a three-dimensional imageable region 411 into which is positioned guide member 133. Parts of vascular wall 406 and vascular blockage 414 are also within imageable region 411 as shown in FIG. 4 given their relative position to transducer array 325.

As forward-looking transducer array 325 is activated, ultrasonic energy waves 419 begin to radiate from intravascular ultrasound probe 320 beyond distal end 327 of elongate carrier body 304 and into and through imageable region 411. Imageable region 411 is external to elongate carrier body 304 and includes the contents of vascular lumen 404, vascular wall 406, vascular blockage 414, and possibly the contents of structures and tissues outside vascular vessel 400. The behavior of each individual transducer within the forward-looking transducer array 325 is coordinated by integrated circuits 317 so that intravascular ultrasound probe 320 operates to image all of imageable area 411 as a three-dimensional region capturing properties of the structures within the region such as volumes, densities, rates of flow of fluids through vascular lumen 404, shapes, sizes, lengths, and other properties of objects found within the region that may be determined. It should be noted that although FIG. 4 indicates an apparent maximum extent of the imageable region 411, no assumption should be made from the illustration as to whether such a maximum range exists, nor to what extent it reaches. Many factors determine the sensory capabilities of an ultrasonic imaging probe in general. Among them are the unique attributes of a particular patient, the particular location within the body relative to various organs and structures, as well as the power and construction of the forward-looking transducer array 325. Thus no particular assumption should be made as to the degree to which imageable region 411 extends beyond distal end 327.

The result of penetrating imageable region 411 with ultrasonic energy and sensing the return echoes is three-dimensional image data 425 indicating various information such as the extent to which vascular blockage 414 extends into vascular lumen 404, the type and density of the material vascular blockage 414 is made of, and various other related information. In order to collect this information, elongate carrier body 110 is coupled to an image data interface device 233 through a transducer link 223 as described above. The data interface device 233 is in turn coupled to image data display device 227 by connecting member 229, also as described above. Return echoes from within imageable region 411 are converted to a data stream by image data interface device 233 and the data is then passed to image data display device 227. The data is then processed into three-dimensional image data 425 and displayed as a three-dimensional image of imageable area 411, or possibly also viewed as a collection of two-dimensional images, or "slices", extracted from the three-dimensional image data 425. The clinician may then view, review, or save the images or the data for the patient to view later, archive in medical records, or use for other purposes.

During the use of guide member 133 shown in FIG. 4, the clinician may introduce elongate carrier body 304 into the body at an appropriate point by various methods depending on the procedure required. The clinician may also introduce guide member 133 through first lumen 311 at the same time, or at another time as well. The precise order of activities used to introduce guide member 133 is unimportant to the use of the system for collecting information. Elongate carrier body 304 is advanced through the body, preferably through a vascular lumen such as a blood vessel, to the area of the body to be imaged by intravascular ultrasound probe 320. This navigation is facilitated by guide member 133 which is often introduced well ahead of elongate carrier body 320 for the purpose of guiding it through the body. The navigation of guide member 133 may also be aided through imaging performed by other means such as by fluoroscopy, MRI imaging, and the like. In many cases it may be advantageous to operate intravascular ultrasound probe 320 to obtain image data as the elongate carrier body 304 is advanced as well.

FIG. 4 illustrates the operation of intravascular ultrasound probe 320 in conjunction with guide member 133. It can be seen in FIG. 4 (as in FIG. 2) that joint 113 is preferably positioned proximally to ultrasonic transducer 320 and is therefore proximal to imageable region 411. By this relative positioning of guide member 133 and intravascular ultrasound probe 320, first guide body portion 130 including echolucent material is the only portion of guide member 133 within imageable region 411. As a result, ultrasonic energy 419 emitted from forward-looking transducer array 325 passes primarily through first guide body portion 130 rather than being substantially reflected by it and therefore first guide body portion 130 does not substantially interfere with image data 425. This result is preferable insofar as it avoids excessive extraneous information appearing within image data 425 that may otherwise obscure important information or make important information more difficult to discern. However, if guide member 133 is positioned with joint 113 distal to forward-looking transducer array 325, extraneous information, "noise," "shadows," or other interference may begin to appear in image data 425 if second guide body portion 103 is composed of echogenic material that blocks the passage of ultrasonic energy 419 through guide member 133 causing it to appear in, or interfere with, resulting image data 425.

As discussed above with regard to FIG. 2, in some cases it may be preferable for the clinician to maintain visual cues within image data 425 indicating the location of the echolucent portion of guide member 133 within vascular lumen 404. This may be especially useful where the clinician is operating an automated imaging system that may rely on the echogenic markers in order to automatically position intravascular ultrasound ultrasonic probe 320. Therefore, as noted above, at least one, and possibly more than one, longitudinally spaced echogenic marker 129 is provided as part of first guide body portion 130 of guide member 133. Echogenic markers 129 may be individual markings or marker regions having groups of markings arranged in various patterns such as a helix, lines, stripes, dots and the like (examples of various embodiments of echogenic markers and marker regions are shown in FIGS. 5A through 7C). Some or all of ultrasonic energy 419 can then pass through the rest of guide member 133 with small amounts being reflected back to ultrasonic transducer array 325 by echogenic markers 129 or optionally by guide member 133 as well depending on its construction. Because of their small size relative to first guide body portion 130, echogenic markers 129 appear in image data 425 and therefore indicate the position of first guide body portion 130 but without causing substantial visual interference. Echogenic markers 129 thereby aid the clinician in maneuvering guide member 133 through vascular lumen 404 by maintaining visual cues within three-dimensional image data 425.

Various types of visual cues may be required depending on a number of factors such as whether the imageable region is two-dimensional or three-dimensional, the location to be imaged within the body, the type of structures to be imaged, and others. Illustrated in FIGS. 5A through 7C are various examples of guide members similar to guide member 133 having various arrangements of echogenic markers and marker regions. In each of these embodiments described in the following FIGS. 5A through 7C, as with echogenic markers 129 shown in FIGS. 1 through 4 above, echogenic markers have various modes of construction. For example an echogenic marker that appears as a ring (such as echogenic marker 129 in FIG. 1 through FIG. 4) may be created by adhering a narrow band of echogenic material such as metal, or other acoustically reflective material, to the exterior surface of the guide member (such as guide member 133 in FIG. 1). Likewise, a similar effect may be achieved by embedding a narrow band of echogenic material within or beneath the surface of the guide member. Other embodiments are also envisioned such as a void within the guide member filled with a vacuum, or a gas such as nitrogen, air, or other gas, or a small piece of echogenic material such as a metal bead, metal flakes, or other echogenic material within the body of the guide member. These various modes of construction can be used together as well in various combinations to create the echogenic markers described.

Figure 5A:
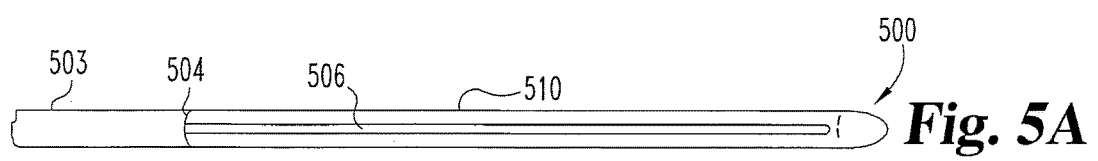
FIG. 5A-7C are perspective views of other embodiments of the guide member shown in FIGS. 1-4.
Figure 5B:
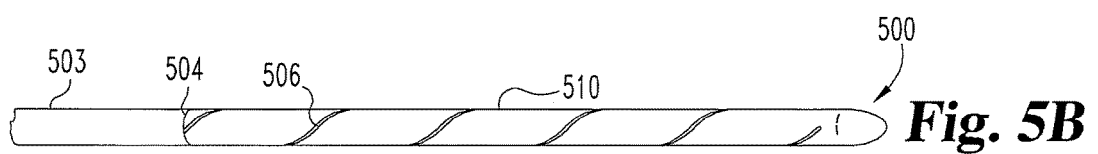
Figure 5C:
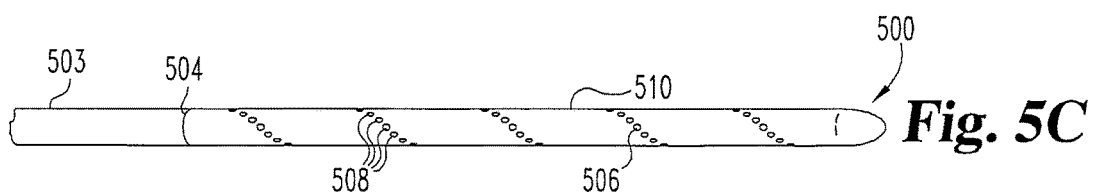

Illustrated in FIGS. 5A, 5B, and 5C, are examples of a guide member 500 having a first guide body portion 510, joined to a second guide body portion 503 at joint 504. A continuous longitudinally extending echogenic marker 506 appears as well. In FIG. 5A, echogenic marker 506 appears as a single continuous unbroken ribbon or band extending along first guide body portion 510 substantially parallel to the longitudinal axis of first guide body portion 510. As described above, echogenic marker 506 may be created by attaching echogenic material to the exterior of guide member 500, by embedding echogenic material within the guide member 500, or by manufacturing guide member 500 with echogenic structures or materials within first guide body portion 510. Other techniques may be used as well for causing echogenic marker 506 to appear during imaging as well. In FIG. 5B, echogenic marker 506 is a single continuous longitudinally extending echogenic marker defining a helical pattern. A similar echogenic marker 506 appears in FIG. 5C comprising a continuous longitudinally extending echogenic marker 506 here embodied as a marker pattern having a pattern of echogenic marker elements 508 separated by discontinuities in the marker material or structure. In this embodiment, each individual echogenic marker element 508 is part of a single echogenic marker 506. Each "dot" (marker element 508) in FIG. 5C may be an individual metal flake, metal bead, gas bubble, or other echogenic material or structure as described above with respect to markers 129.

Figure 6A:
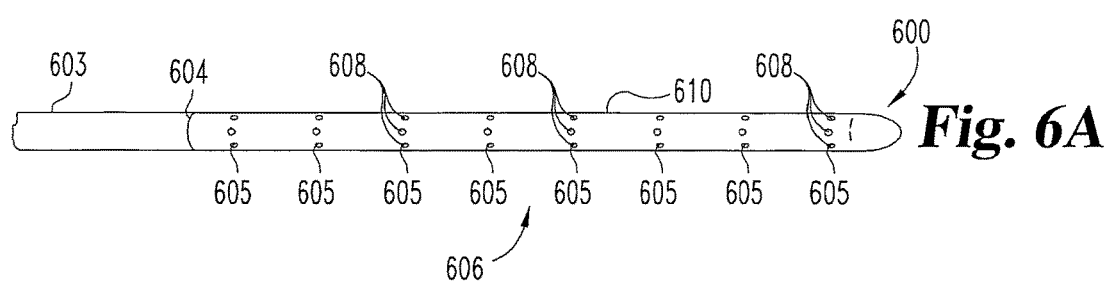
Figure 6B:
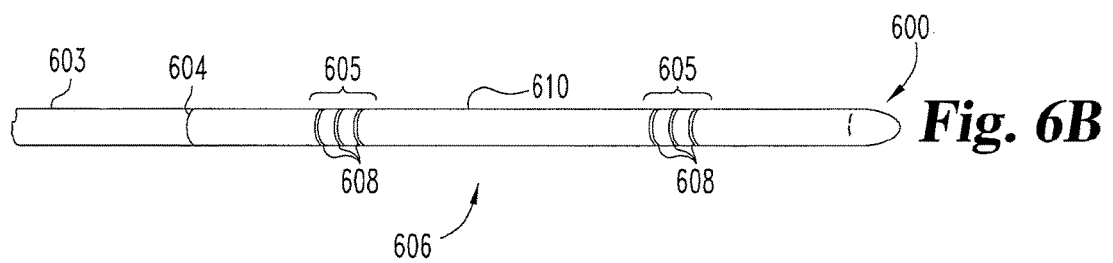
Figure 6C:
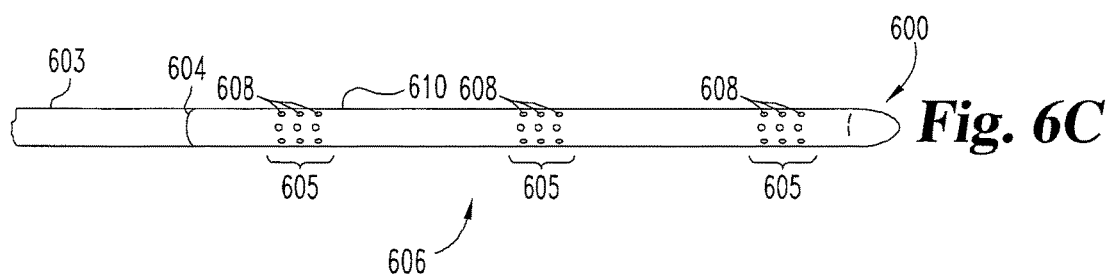

In FIGS. 6A, 6B, and 6C, guide member 600 is illustrated having a first guide body portion 610 with an echogenic marker 606 embodied as a marker pattern with one or more longitudinally spaced echogenic marker regions 605. Marker regions 605 include one or more echogenic marker elements 608. Similar to previously mentioned embodiments, first guide body portion 610 is joined to a second guide body portion 603 at joint 604. As illustrated, marker elements 608 may be separated from one another by discontinuities in the echogenic material or structure. Each of the individual marker elements 608 are constructed as discussed above with respect to marker elements 508 and markers 129. Each individual echogenic marker element 608 in FIG. 6A can therefore be thought of as an echogenic "dot". In FIGS. 6B and 6C, each individual echogenic marker element 608 is an echogenic ring, or individual dots arranged annularly in one or more ring patterns within each marker region 605.

Figure 7A:
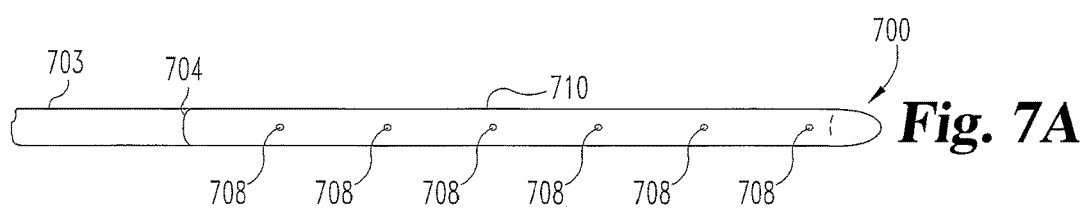
Figure 7B:
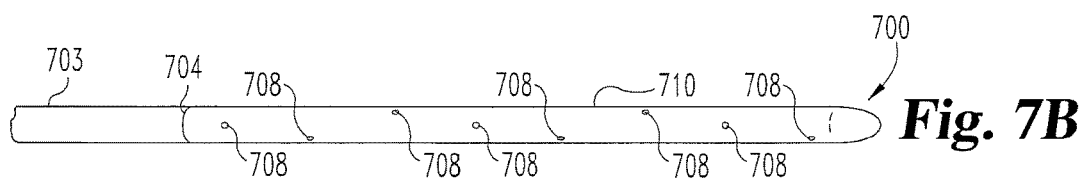
Figure 7C:
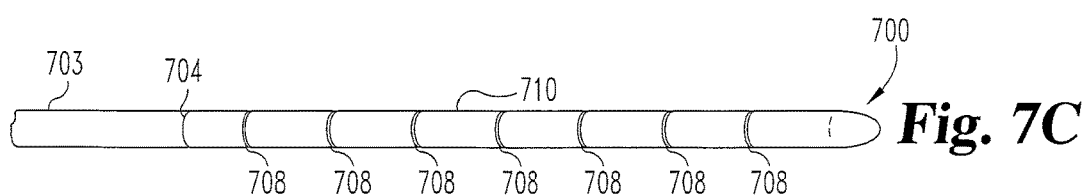

FIGS. 7A, 7B, and 7C also illustrate various arrangements of discrete echogenic markers 708 spaced along a first guide body portion 710 of a guide member 700 also having a second guide body portion 703 joined to the first guide body portion 710 at joint 704. In FIGS. 7A and 7B, multiple echogenic markers 708 are illustrated as individual echogenic "dots" as discussed above. In FIG. 7B, the echogenic markers 708 are positioned in a helical marker pattern rather than in a straight line shown in FIG. 7A. In FIG. 7C, each echogenic marker 708 is a configured as a band disposed around at least a portion of the perimeter or circumference of guide member 700. As with FIG. 5C, each "dot" or ring illustrated in FIG. 7A through 7C indicates an individual echogenic marker 708 formed from an echogenic substance or structure as described above such as a ring of metal, solid bead of metal, a bubble of air, metal flake, or void filled with a gas, a vacuum, or other echogenic substance.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. An intravascularly-introducible apparatus, comprising:
    an elongate carrier body for intravascular passage, the carrier body defining at least one lumen and carrying at least one intravascular ultrasound probe for generating image data representing an imageable region external of the carrier body; and
    a guide member having an elongate guide body receivable through said lumen, the elongate guide body having at least a first guide body portion capable of passage into said imageable region;
    wherein said first guide body portion includes an echolucent material and has associated therewith at least one echogenic marker.

2. The apparatus of claim 1, wherein elongate guide body comprises at least two longitudinally-extending guide body portions joined to one another.

3. The apparatus of claim 2, further comprising:
    a second guide body portion formed of an echogenic material;
    wherein said elongate guide body includes at least said first guide body portion joined to said second guide body portion.

4. The apparatus of claim 2, wherein the first guide body portion includes a polymeric material, and the second guide body portion includes a metal.

5. The apparatus of claim 1, wherein the at least one echogenic marker includes a plurality of longitudinally spaced echogenic marker regions.

6. The apparatus of claim 1, wherein the at least one echogenic marker includes a plurality of discrete echogenic markers or a continuous longitudinally-extending echogenic marker.

7. The apparatus of claim 6, wherein the at least one echogenic maker includes said continuous longitudinally-extending echogenic marker, and wherein the longitudinally-extending echogenic marker defines a helical pattern.

8. The apparatus of claim 1, wherein the elongate carrier body is a catheter.

9. The apparatus of claim 1, wherein the imageable region is a substantially two-dimensional cross-sectional slice.

10. The apparatus of claim 1, wherein the imageable region is three-dimensional.

11. The apparatus of claim 1, wherein the imageable region includes a region forward of the ultrasound probe.

12. The apparatus of claim 1, wherein the first guide body portion includes a polymeric material having a density in the range of 0.5 grams/cc to 3.5 grams/cc.

13. The apparatus of claim 1, wherein the first guide body portion includes polyetheylene having a density in the range of about 0.8 grams/cc to about 1.1 grams/cc.

14. The apparatus of claim 1, wherein the at least one echogenic marker is fixed to or within an outer surface of the guide body portion so that the at least one echogenic marker faces a wall of the lumen of the carrier body and is movable with respect to the carrier body.

15. The apparatus of claim 1, further comprising an ultrasonic transducer for emitting ultrasonic energy.

16. The apparatus of claim 15, wherein the ultrasonic transducer is part of an ultrasound probe separate from the guide member and at least partially within the carrier body.

17. The apparatus of claim 16, wherein the carrier body includes a second lumen separate from the lumen through which the elongate guide body is receivable, and wherein the ultrasound probe extends through the second lumen and is movable with respect to the carrier body and with respect to the guide member.

18. The apparatus of claim 17, wherein the elongate guide body comprises first and second guide body portions that extend longitudinally along a common axis, and wherein the first and second guide body portions are joined at a joint, and wherein the ultrasonic transducer is positioned distal to the joint so that when the ultrasonic transducer is used, ultrasonic energy emitted from the ultrasonic transducer passes through the first guide body portion but not through the second guide body portion.

* * * * *